United States Patent [19]

Cunningham et al.

[11] Patent Number: 5,134,076
[45] Date of Patent: Jul. 28, 1992

[54] MONOCLONAL ANTIBODIES SPECIFIC FOR PROTEASE NEXIN-1 AND PURICIATION OF PROTEASE NEXIN-1 USING MONOCLONAL ANTIBODIES

[75] Inventors: Dennis D. Cunningham, Laguna Beach; Steven L. Wagner, Laguna Hills; William E. Van Nostrand, Irvine, all of Calif.

[73] Assignee: The Regents of the University of California, Berkeley, Calif.

[21] Appl. No.: 249,787

[22] Filed: Sep. 27, 1988

[51] Int. Cl.$^5$ .................... C12N 5/20; C07K 15/28; C07K 3/20; C12P 21/08
[52] U.S. Cl. .................... 435/240.27; 530/388.25; 530/413; 435/70.21; 435/172.2
[58] Field of Search .................... 530/387, 413, 388.25; 435/240.27, 70.21, 172.2

[56] References Cited

FOREIGN PATENT DOCUMENTS 0233838  8/1987  European Pat. Off.
0251505  1/1988  European Pat. Off.

OTHER PUBLICATIONS

Kipps et al., "Handbook of Experimental Immunology" vol. 4, Weis et al., Eds. Blackwell Sci. Publ., 1986.
Howard et al., J. Biol. Chem. 261(2): 684-689, Jan. 15, 1986.
Eaton et al., J. Biol. Chem. 259(10): 6241-6247, May 25, 1984.
Gloor et al., Cell 47:687-693, Dec. 5, 1986.
Wagner et al. Biochemistry 27: 2173-2176, Mar. 22, 1988.
Cunnmingham, D. et al., J. Cellular Biochem. 32:281-291 (1986).
Gurwitz, D., and D. Cunningham, Proc. Natl. Acad. Sci. U.S.A., 85:3440-3444 (1988).
Wagner, S. et al., Nature, (submitted).
Scott, R. and J. Baker, J. Biol. Chem. 258:10439-10444 (1983).
Scott, R. et al., J. Biol. Chem. 260:7029-7034 (1985).
Farrell, D. et al., Biochem. J. 237:907-912 (1986).
Van Nostrand et al., Biochemistry 27:2176-2181 (1988).
Kearney, J. et al., J. Immunol. 123:1548-1550 (1979).
Rosenberg, R. and P. Damus, J. Biol. Chem. 248:6490-6505 (1973).
Tollefsen et al., J. Biol. Chem. 257:2162-2169 (1982).
Sim et al., Biochem. Biophys. Acta 612:433-449 (1980).
Beatty et al., J. Biol. Chem. 255:3931-3934 (1980).
Van Nostrand, W. and D. D. Cunningham, J. Biol. Chem. 262:8508-8514 (1987).
Laemlli, U., Nature 227:680-685 (1970).

*Primary Examiner*—John J. Doll
*Assistant Examiner*—Paula Hutzell
*Attorney, Agent, or Firm*—Knobbe Martens Olson & Bear

[57] ABSTRACT

Monoclonal antibodies having a specificity for protease nexin-1 are described. Preferably an antibody has specificity to the reactive protease-binding site. The antibody is used in the affinity purification of PN-1 to produce large quantities of substantially pure PN-1, free of other biologically active molecules. Over a 2000-fold purification of a crude preparation of PN-1 may be obtained. The affinity-purified PN-1 is suitable for use in pharmacological preparations used in the treatment of neurological disease associated with serine protease-mediated inhibition of regenerative processes.

2 Claims, No Drawings

MONOCLONAL ANTIBODIES SPECIFIC FOR PROTEASE NEXIN-1 AND PURICIATION OF PROTEASE NEXIN-1 USING MONOCLONAL ANTIBODIES

GOVERNMENT INTEREST IN INVENTION

This invention was made with Government support under Grant Nos. GM 31609 and CA 09054 awarded by the Department of Health and Human Services. The Government has certain rights in this invention.

FIELD OF THE INVENTION

This invention relates to the preparation of commercially large quantities of a biological protein, and specifically to the preparation of highly purified protease nexin-1 (PN-1) that is substantially free of other biologically active molecules.

STATEMENT OF DEPOSIT

A cell line corresponding to embodiment of the present invention, and denoted strain mABp9 has been deposited in the American Type Culture Collection, 12301 Parklawn Drive, Rockville, Md., U.S.A. 20852 (Under ATCC No. HB9815) on Sep. 7, 1988, prior to the filing of this application.

BACKGROUND OF THE INVENTION

The interactions of serine proteases and protease nexins appear to play key roles in the regulation of cell growth and development in the tissues. Serine proteases are proteolytic enzymes having a reactive serine at the catalytic site. The presence of a nucleophilic group on the serine residue confers a general substrate specificity on this group of enzymes. Significant serine proteases comprise trypsin, chymotrypsin, thrombin, urokinase, plasmin, and elastase. Protease nexin-1 (PN-1) is a 45 kilodalton protein secreted by a variety of cultured cells, including human fibroblasts. PN-1 controls protease activity in the immediate environment of the cells, rapidly inhibiting the serine proteases, e.g., thrombin, urokinase and plasmin, by covalently binding to a serine group at the catalytic site. The complexes thus formed then bind back, by means of the PN portion of the complex, to the cells where they are internalized and degraded. This inhibition of protease enzymes modulates the response of the cell to the mitogenic effect of thrombin, and limits extracellular proteolysis and matrix degeneration mediated by urokinase (Cunningham, D. et al., J. Cellular Biochem. 32:281-291, 1986). The specificity of PN-1 is narrowed by binding to the extracellular matrix which accelerates its inhibition of thrombin and blocks its inhibition of urokinase and plasmin.

PN-1 is found to have a neurotrophic effect that appears to depend on its inhibition of thrombin. Neuroblastoma cells, as well as several types of primary neuronal cells in culture, rapidly extend neurites, (a morphological indication of differentiation) when switched from serum-containing to serum-free media. However, very low concentration of thrombin (2 nM) can cause cells in serum-free media to retract their neurites. It is presumably the presence of thrombin (and possibly other serine proteases) in serum-containing media that maintains neuroblastoma cells in a non-differentiated state.

In neural tissue, glial cells produce a neurite-stimulating factor which is a protease inhibitor with the same deduced amino acid sequence as PN-1. Both purified PN-1 and serum-free media conditioned by glioma cells promote neuroblastoma differentiation that can be blocked by added thrombin. Gurwitz, D., and D. Cunningham, Proc. Natl. Acad. Sci. USA, 85:3,440-3,444 (1988).

Recent studies on the brain tissues of patients with Alzheimer's disease indicate that an imbalance between proteases and protease nexin-1 may be involved in the etiology of the disease (Wagner, S. et al., Nature, submitted). The proposed pathological process implies that similar imbalances may occur in other neurological diseases, or when neural tissue is injured, so that abnormal amounts of serine protease are present in the tissues. Such imbalances could be corrected by providing PN-1 to complex these proteases so as to inhibit its repression of neural differentiation. However, present methods of isolation are not capable of producing PN-1 appropriately pure for these therapeutic uses.

Previously, PN-1 has been purified according to conventional techniques. One of these takes advantage of a heparin binding site on PN-1, and one step of the procedure involves fractionation over a heparin affinity resin or a resin with a similar affinity ligand, such as dextran sulfate. (Scott, R. and Baker, J. J. Bio. Chem. 258:10,439-10,444 (1983); Scott, R. et al., J. Bio. Chem. 260:7,029-7,034 (1985); and Farrell, D. et al., Biochem. J. 237:907-912 (1986)). During this purification step, other proteins with heparin binding sites can co-purify with PN-1 and contaminate the preparation.

It is therefore an object of the invention to provide highly specific monoclonal antibodies which can be used to purify PN-1 and so provide substantially pure protease inhibitor which is free of other biologically active molecules, and which can be a safe and effective agent for treating neurological diseases related to reduced levels of PN-1 in neural tissues.

BRIEF SUMMARY OF THE INVENTION

The present invention comprises continuous cell lines producing and secreting antibodies specific for PN-1 which comprise fused cell hybrids derived from PN-1 vertebrate antibody-producing cells and cancer cells. In one preferred embodiment, the cell lines are murine hybridomas. One such line strain mAbp9, is deposited with the American Type Culture Collection under accession number HB9815.

The invention also covers all murine hybridoma cells producing antibodies specific for PN-1.

Monoclonal antibodies specific for PN-1 are also within the scope of the present invention. The deposited hybridoma produces a preferred monoclonal mAb9.

In accordance with another aspect of the present invention, there are provided monoclonal antibodies having a specificity for the protease binding site of PN-1 and capable of blocking the binding of a protease thereto, and particularly capable of blocking the binding of thrombin thereto. mAbp9 is such an antibody.

The present invention also includes a method for producing monoclonal antibodies specific for human PN-1, comprising the steps of immunizing an animal with human PN-1; harvesting an antibody-producing organ from the immunized animal; preparing antibody-producing cells from the organ; fusing the antibody-producing cells with cultured cancer cells; selecting hybrid cells which produce monoclonal antibody specific for PN-1; periodically subculturing or otherwise maintaining the hybrid cells so that they reproduce perpetually; and harvesting monoclonal antibodies specific for PN-1 produced by the hybrid cells.

In accordance with still another aspect of the present invention, there is provided a method for preparing substantially pure PN-1, comprising the steps of contacting a crude liquid preparation of the protease nexin-1 with an immobilized monoclonal antibody to the protease nexin-1; separating the liquid preparation from the immobilized antibody; and thereafter eluting the protease nexin-1 in purified form from the immobilized antibody. The immobilized antibody preferably has a specificity for the protease-binding site of protease nexin-1. Also covered by the present invention is purified protease nexin-1 prepared in accordance with the foregoing method.

In accordance with still another embodiment of the present invention, there is provided a method for preparing a pharmaceutical formulation comprising substantially pure protease nexin-1, comprising the steps of contacting a crude liquid preparation of the protease nexin-1 with an immobilized monoclonal antibody to the protease nexin-1; separating the liquid preparation from the immobilized antibody; thereafter eluting the protease nexin-1 in purified form from the immobilized antibody; and combining an effective quantity of the substantially pure protease nexin-1 with a pharmaceutically acceptable carrier.

These and other advantages and features of the present invention will become more fully apparent from the following description and appended claims.

DETAILED DESCRIPTION OF THE INVENTION

The invention provides a technique for preparing a large commercial quantity of PN-1 that is virtually free of other biologically active molecules. A unique feature of the procedure is the use of a highly specific affinity chromatography procedure that depends on the binding of PN-1 to anti-PN-1 monoclonal antibodies (mAbs) as the final step of the purification.

According to the scheme of the procedure, a crude source fluid containing PN-1 is first fractionated using, in a preferred embodiment, dextran sulfate-Sepharose. Alternatively, the PN-1-containing mixture can be fractionated using heparin-Sepharose. Then, the PN-1 from this preliminary purification is bound to anti-PN-1 mAbs immobilized on Sepharose. Substantially pure PN-1 is eluted with a buffer at about pH 3.0.

In the preliminary purification, on either heparin-Sepharose or dextran sulfate-Sepharose, PN-1 is separated from a related form, L-PN-1. The two forms are distinguished from one another by functional differences. PN-1, which is produced in greater concentration in conditioned cell medium, has a higher affinity for heparin. Heparin accelerates the rate of inactivation of thrombin by PN-1 and L-PN-1 to same the degree; however, in the presence of fixed fibroblasts, the rate of complex formation with L-PN-1 is stimulated approximately 2-fold., whereas the rate with PN-1 is increased nearly 5-fold. Aside from this difference, several structural and functional comparisons between L-PN-1 and PN-1 indicate there are no significant differences. The molecular weights of L-PN-1 and PN-1 as well as their complexes with proteases cannot be distinguished by SDS-PAGE. Both L-PN-1 and PN-1 complex the same proteases. $^{125}$I-thrombin L-PN-1 complexes and $^{125}$I-thrombin PN-1 complexes both bind to fibroblasts and their binding is blocked in the presence of heparin (Van Nostrand et al., Biochemistry 27:2,176–2,181 (1988)).

Most importantly for the purposes of this invention, both PN-1 and L-PN-1 molecules are recognized equally by the anti-PN-1 mAbs tested. Therefore, the mAb Sepharose purification step is equally effective at purifying either PN-1 or L-PN-1 to homogeneity in an immunoaffinity step. For the same reason, the immunoaffinity step cannot discriminate between the two molecules. However, because L-PN-1 has a lower affinity for heparin, the dextran sulfate-Sepharose (or heparin-Sepharose) step completely separates it from PN-1. By means of a combination of the two procedures, both L-PN-1 and PN-1 can be purified to apparent homogeneity. The method provides a purification of milligram quantities of physiologically effective PN-1, sensitive to heparin modulation in vivo, and concentrated over 2,000-fold from the crude source. It is therefore suitable for use in pharmacological preparations in which pure and potent PN-1 may be used in treating neurological disorders related to reduced levels of PN-1 or L-PN-1 in neural tissues.

PREPARATION OF HYBRIDOMAS

Hybridomas producing monoclonal antibody to PN-1 were prepared using reagents and instructions supplied in the form of a kit (HyBRL Prep Kit) from Bethesda Research; Labs, Bethesda, Md. PN-1 used for immunizations was purified by the dextran sulfate-Sepharose affinity chromatographic procedure as described by Farrell, et al., Biochem. J. 237:907–912 (1986).

The production of anti-PN-1 mAbs focused on their ability to block the inhibition of target protease. Antibodies that block these reactions are valuable in isolating protease-inhibiting PN-1, as well as probing its physiological roles. To increase the chances of obtaining blocking mAbs, mice were immunized with both native and denatured PN-1 with the expectation that this might increase the number of PN-1 epitopes available to their immune system.

Eleven week old female BALB/c mice were immunized intraperitoneally with PN-1 (50 μg emulsified in 0.2 ml of Freund's complete adjuvant) every week for a period of five weeks. Four days after the last immunization, the mice were injected in the tail vein with 25 μg of PN-1 dissolved in 0.2 mL of phosphate-buffered saline (PBS). Three days later, splenocytes ($1.1 \times 10^8$ cells) from an immunized mouse were fused with $2.8 \times 10^7$ myeloma cells from a non-secreting mouse myeloma, P3X63-Ag8.653 (Kearney, J. et al., J. Immunol. 123:1,548–1,550 (1979)), purchased from the American Type Culture Collection, Rockville, Md. The procedures employed were as described in the instruction manual provided with the HyBRL Prep Kit, except that poly (ethylene glycol) 1540 (Sigma, St. Louis, Mo.) was used to fuse the cells. Specifically, $2.8 \times 10^7$ myeloma cells (P3X63-Ag8.653) were suspended in 10 ml of Dulbecco's modified Eagle's Medium (DMEM) (serum free) and were incubated with a suspension of splenocytes ($1.11 \times 10^8$ in 10 ml serum free DMEM). The combined cell suspension was centrifuged for 5 min. at $200 \times g$. The supernatant was decanted and the cell pellet was carefully drained. The cell pellet was then resuspended in residual medium by tapping the bottom of the tube on the benchtop. Exactly 0.7 ml of 50% poly(ethylene glycol) 1540 (Polysciences) was added to the cell pellet over a 1 min. time period. The 50% PEG solution was prepared in a quantity of 10 ml and consisted of 5 ml of PEG 1540, 4.5 ml serum free DMEM, and 0.5 ml DMSO. The PEG solution was warmed to 37° C. prior to use. After adding the PEG solution, the cell pellet was swirled gently for 1 min. During the next minute, 0.7 ml of DMEM containing 15% fetal calf serum (growth medium) was added. Another 0.7 ml of the growth medium was added during the next minute. Finally, 5.6 ml of growth medium was added over the next 2 minutes. The fusion mixture was then centrifuged for 5 min. at 130×g. The pelleted cells were then gently resuspended in 15.4 ml of HAT (hypoxanterin, aminopterin, and thymidine) medium. The HAT medium consisted of 500 ml of growth medium plus 10 ml of 50×HAT (Bethesda Research Laboratories). The resuspended cells were aliquoted into 96-well tissue culture plates (Falcon) and grown. A total of 293 wells contained hybridomas, which were visible after a two week period.

Screening Hybridomas

Approximately 21 days after fusion, hybridoma supernatants were tested for the production of antibody to PN-1. Hybridomas which secreted antibodies specific for PN-1 were detected by a solid phase enzyme-linked immunosorbent assay (ELISA) using the Streptavidin HyBRL Screen Kit (Bethesda Research Laboratories, Bethesda, Md.) with minor modification. 100 μl of PBS containing 100 ng of PN-1 were added to each well of 96-well microliter plates for 2 h at 37° C. Unbound antigen was removed by rinsing the wells three times with PBS. The wells were then filled with PBS containing 1.0% ovalbumin, incubated 30 min at 25° C., and rinsed three times with 0.05% Tween 20 in PBS. Hybridoma supernatant (50 μl) was added to each well and incubated for 60 min at 37° C. with constant agitation. Then, the wells were rinsed four times with 0.05% Tween 20 in PBS and 50 μl of biotinylated goat anti-mouse IgG (Cappel Laboratories, Malvern, Pa.), 1:1000 dilution in PBS containing 1.0% ovalbumin was added. The biotinylated antibody was removed and the wells were rinsed as above. Then, 50 μl of streptavidin horseradish peroxidase conjugate (Amersham, Arlington Heights, Ill.), 1:1000 dilution as above, was added to each well; the microtiter plates were shaken for 30 min at 37° C. The wells were then rinsed five times as above and once with PBS and stained with 100 μl of the peroxidase substrate solution (10 mM o-phenylenediamine, 0.012% $H_2O_2$, 100 mM sodium citrate, pH 4.5). After approximately 30 min the peroxidase activity was quenched by adding 50 μl of 4N $H_2SO_4$ to each well. The absorbance at 492 nm was recorded with a Titertek Multiscan ELISA reader (Flow Laboratories, McLean, Va.). For a control, the ELISA was carried out as above but in the absence of PN-1 to measure nonspecific antibody binding.

Isolation and Properties

The positive hybridomas were cloned by limiting dilutions at an average cell density of 0.5 to 1 cell per well using $10^5$ splenocytes/well as the feeder layer. Positive monoclonal cultures were expanded into 24 well plates and then into 25 $cm^2$ tissue culture flasks. Cells from confluent 25 $cm^2$ flasks were then injected intraperitoneally into mice which had been primed with 0.25 ml of pristine 3-14 days prior to inoculation to promote formation of antibody-rich ascites fluid.

Cloning by limiting dilution resulted in 21 stable monoclonal hybridoma lines which secreted anti-PN-1.

All 21 mAbs were shown to be specific for PN-1 by ELISA. Antibody subclasses for each of the monoclonal hybridoma lines were identified with a Hybridoma Sub-Isotyping Kit (Behring Diagnostics, La Jolla, Calif.). These studies showed that each cell line secreted only one class of immunoglobulin. The mAbs were purified by using an Affi-Gel Protein A MAPS II Kit (Bio-Rad, Richmond, Calif.), and their concentration determined spectrophotometrically using an extinction coefficient (1% w/v; 1 cm) of 14 (Ey et al., Immunochemistry 15:429–436 (1978). Four of these antibodies exhibited superior properties, mAbp1, mAbp6, mAbp9, and mAbp18. One preferred antibody is mAbp9, and the strain producing that antibody has been deposited with ATCC, as previously stated.

To determine the uniqueness of the PN-1 epitopes recognized by the mAbs, the ability of all 21 mAbs to cross-react with 4 plasma inhibitors of serine proteases was tested. The ELISA response for all 21 mAbs increased with increasing concentrations of PN-1 but showed no detectable binding to 1 μg of antithrombin III (Rosenberg, R. and Damus, P., J. Bio. Chem. 248:6,490–6,505 (1973), heparin cofactor II (Tollefsen et al., J. Bio. Chem. 257:2,162–2,169 (1982), Cl inhibitor (Sim et al., Biochim. Biophys. Acta 612:433–449 (1980), or α-protease inhibitor (Beatty et al., J. Bio. Chem. 255:3,931–3,934 (1980).

Preparation of PN-1

Both LPN-1 and PN-1 were purified from serum-free medium conditioned by human fibroblasts. The human fibroblasts were isolated from explants of neonatal foreskins and were maintained in Dulbecco;s modified Eagle's medium (DMEM) containing 10% bovine serum as described by Baker et al., Cell (Cambridge, Mass.) 21:37–45 (1980). Three-liter microcarrier cultures of the fibroblasts were prepared employing gelatin microcarrier beads as described by Van Nostrand, W. and Cunningham, D., J. Biol. Chem. 262:8,508–8,514 (1987).

To collect serum-free conditioned medium, the microcarrier beads were allowed to settle from the cultures, and the serum-containing medium was removed by aspiration. It was replaced with 2 L of DMEM buffered with 20 mM HEPES, pH 7.4, containing 100 units/mL penicillin and 100 μg/mL streptomycin. The microcarrier beads were again allowed to settle, and then the rinse medium was removed by aspiration and replaced with 2 L of DMEM buffered with 20 mM HEPES, pH 7.4, containing the antibiotics and 0.1% bovine serum albumin. The microcarrier culture was maintained in this medium for 24 h at 37° C. with stirring. This medium was then removed, and the cultures were incubated with fresh serum free medium containing bovine serum albumin for two subsequent 3-day periods. After each period, the "conditioned" medium was collected. Using two 3-L microcarrier cultures, 4 L of serum-free conditioned media were harvested on each collection day. The cells were then returned to culture medium containing 5% bovine serum for 5 to 7 days after which they were cycled again for collection of serum-free conditioned medium. The serum-free conditioned medium was aspirated into a siliconized flask, filtered to remove particulates, and chilled to 4° C. Phenylmethanesulfonyl fluoride, butylated hydroxytoluene, and sodium azide were added to final concentrations of 200 μM, 50 μM, and 0.04% respectively. Conditioned medium was used within 24 hours after collection. All subsequent chromatographic steps were conducted at 4° C.

Four liters of serum-free conditioned medium was applied to a column (2.5×40 cm) of dextran-sulfate-Sepharose, and equilibrated with phosphate-buffered saline at a flow rate of 100 mL/h. After the column was loaded, it was washed with phosphate-buffered saline until the $A_{280}$ returned to baseline. The adsorbed protein was eluted from the column with a 1.5-L linear gradient from 0.15 to 1.2 M NaCl in phosphate-buffered saline, and fractions of 20 mL were collected. Fractions containing L-PN-1 or PN-1 were identified by incubation with $^{125}$I-thrombin and subsequent analysis by SDS-PAGE and autoradiography as described in Example 2.

Final purification of L-PN-1 and PN-1 was achieved by immunopurification with a mAbp9-Sepharose column. Pooled fractions containing either L-PN-1 or PN-1 were applied to the monoclonal antibody column followed by washing with 1 M NaCl. The adsorbed L-PN-1 or PN-1 was then eluted from the column with a glycine hydrochloride buffer at pH 3.0. Approximately 70% of the total starting PN-1-like activity in the conditioned medium was recovered after the dextran sulfate-Sepharose and immunoaffinity steps. Also, L-PN-1 represented approximately 20% of the total recovered protein an activity.

EXAMPLE 1

Screening mAbs for Ability to Inhibit Formation of PN-1-Protease Complexes

The ability of four purified mouse mAbs (mAbp1, mAbp6, mAbp9, and mAbp18) to block formation of 125I-thrombin-PN-1 complexes was assessed.

PN-1 (0.2 μM) was incubated for 60 min at 37° C. with various concentrations (0.02–4.0 μM) of either mAb or polyclonal antibody in PBS containing 0.01% bovine serum albumin in a volume of 20 μl. In some experiments, heparin (0.2 mM final concentration) was incubated with PN-1 prior to addition of antibody. Following the antibody incubation, a 5 μl aliquot of $^{125}$I-protease (diluted in 0.01% bovine serum albumin) was added to each tube and incubated with the PN-1 antibody solution for 15 min. at 37° C. The final concentration of $^{125}$I-protease was 0.04 μM. The specific activities of the various proteases were 25,000 cpm/ng for thrombin and trypsin and 13,400 cpm/ng for urokinase. The reaction was quenched by adding 25 μl of Laemlli SDS-polyacrylamide gel sample dilution buffer. The individual samples were run on 7.5% SDS-polyacrylamide gels according to Laemlli, U., Nature 227:680–685 (1970). Autoradiograms were then prepared from the gels. To quantitate protease-PN-1 complexes, the autoradiograms were aligned with the dried gels, the $^{125}$I-labeled complexes were excised from the gels, and radioactivity was measured in a gamma counter.

Neither rabbit polyclonal IgG nor mAbp1 inhibited $^{125}$I-thrombin-PN-1 complex formation over the concentration ranges studied (up to 20-fold molar excess), indicating that these bind to epitopes which are remote from the crucial thrombin interactions sites on PN-1. In contrast, mAbp6, mAbp9, and mAbp18 completely inhibited $^{125}$I-thrombin-PN-1 complex formation at stoichiometric mAb and PN-1 concentrations.

Similar results were obtained with urokinase: mAb6, mAb9, and mAb18 blocked formation of $^{125}$I-urokinase-PN-1 complexes at stoichiometric concentrations of mAb and PN-1, while mABp1 did not block this reaction. Monoclonal antibodies mAbp6 and mAbp9 equally inhibited $^{125}$I-trypsin-PN-1 complex formation, although a molar ratio of mAb to PN-1 of 5.0 was required for complete inhibition. In contrast, mAbp18 blocked formation of PN-1 complexes with $^{125}$I-trypsin at stoichiometric mAb and PN-1 concentrations as described above for thrombin and urokinase.

Overall mAbp9 is a preferred antibody, and the hybridoma producing that antibody has been deposited

EXAMPLE 2

Assay for PN-1-like Activity

To assay fractions from the dextran sulfate chromatographic procedure for PN-1 or L-PN-1, aliquots of the collected fractions were incubated with known quantities of 125I-thrombin for 20 min at 37° C. An equal volume of SDS-PAGE sample buffer was then added, and the mixtures were subjected to SDS-PAGE. After autoradiography, PN-1-like activity was monitored by the presence of an 80-kDa complex with $^{125}$I-thrombin. To quantitate PN-1 activity, the autoradiograms were aligned with the dried gels, and the 80kDa $^{125}$I-thrombin-PN-1 or $^{125}$I-thrombin-L-PN-1 complexes were located, excised, and measured in a gamma counter.

A similar assay was used to quantitate PN-1 and L-PN-1 activity from the monoclonal antibody-Sepharose chromatography; however, in these measurements, pooled fractions from each step were compared to purified PN-1. One PN-1 unit is defined as the amount of $^{125}$I-thrombin complexed by 10 pmol of standardized PN-1 as previously described by Farrell, et al., Biochem. J. 237:907–912 (1986).

EXAMPLE 3

Monoclonal Antibody-Sepharose Chromatography

A monoclonal antibody (mAbp9) that bound PN-1 was isolated, purified, and characterized as described. It was coupled to CNBr-activated Sepharose 4B as described by the manufacturer (Pharmacia, Piscataway, N.J.). During the purification, mAbp9 did not detectably bind proteins other than PN-1 or L-PN-1. Pooled fractions containing L-PN-1 or PN-1 from dextran sulfate-Sepharose were individually applied to a column (0.5×10 cm) of mAbp9-Sepharose equilibrated with 20 mM potassium phosphate/1M NaCl, pH 7.4, at a flow rate of 10 mL/h. After the column was loaded, it was washed with 5 column volumes of 20 mM potassium phosphate/1M NaCl, pH 7.4, followed by 2 column volumes of 20 mM potassium phosphate/1M NaCl, pH 7.4. The adsorbed L-PN-1 or PN-1 was eluted from the column with 0.2 M glycine hydrochloride/0.15 M NaCl, pH 3.0. One-milliliter fractions were collected in tubes containing 100 μL of 2 M Tris-HCl, pH 8.3, to neutralize the elution buffer. Concentrations of purified L-PN-1 or PN-1 were determined by their absorbance at 280 nm by using the specific absorption coefficient A=16.2 (Scott et al., J. Biol. Chem. 260:7,029–7,034 (1985).

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced with their scope. It should be specifically noted that the term "protease nexin-1" and "PN-1" are intended, in the claims, to include the corresponding L-PN-1 moiety.

What is claimed is:

1. Hybridoma strain ATCC No. HB9815.
2. Monoclonal antibody mAbp9 produced by the hybridoma having ATCC Accession No. HB9815.

* * * * *